(12) United States Patent
Giraud et al.

(10) Patent No.: US 7,252,964 B2
(45) Date of Patent: Aug. 7, 2007

(54) ISOLATED CAROTENOID BIOSYNTHESIS GENE CLUSTER INVOLVED IN CANTHAXANTHIN PRODUCTION AND APPLICATIONS THEREOF

(75) Inventors: Eric Giraud, Castelnau le Lez (FR); Laure Hannibal, Montpellier (FR)

(73) Assignee: Institut de Recherche pour le Developpement (I.R.D.), Paris, Cedex (FR)

( * ) Notice: Subject to any disclaimer, the term of this patent is extended or adjusted under 35 U.S.C. 154(b) by 634 days.

(21) Appl. No.: 10/166,037

(22) Filed: Jun. 11, 2002

(65) Prior Publication Data

US 2003/0087337 A1    May 8, 2003

Related U.S. Application Data

(60) Provisional application No. 60/297,272, filed on Jun. 12, 2001.

(51) Int. Cl.
*C12P 23/00*    (2006.01)

(52) U.S. Cl. .................. 435/67; 435/69.1; 435/320.1; 435/252.3; 435/254.11; 435/325; 435/419; 536/23.1; 536/23.2; 536/23.7; 530/350

(58) Field of Classification Search .............. 536/23.2, 536/23.7; 435/320.1, 252.3, 254.11, 325, 435/419

See application file for complete search history.

(56) References Cited

U.S. PATENT DOCUMENTS 5,965,795 A * 10/1999 Hirschberg et al. ......... 800/295

OTHER PUBLICATIONS

Harker et al. Biosynthesis of ketocarotenoids in transgenic cyanobacteria expressing the algal gene for beta-C-4-oxygenase, crtO. FEBS Letters (1997) 404:129-134.*
Mann et al. GenBank Accession No. CAB56040. phytoene desaturase [Nostoc sp. PCC 7120]. (1999).*
Omura et al. GenBank Accession No. BAB69140. phytoene desaturase [*Streptomyces avermitilis*]. (2001).*
Schumann et al. GenBank Accession No. AAA91950. phytoene desaturase. (1996).*
Harker et al. GenBank Accession No. Y15112. *Paracoccus marcusii* crtW, crtZ, crtY, crtI, crtB, & crtE genes. (1999).*
Moluba et al., Applied and Environmental Microbiology, Jul. 1999, vol. 65, No. 7, pp. 3084-3094.*
Lorquin et al., Applied and Environmental Microbiology, Mar. 1997, vol. 63, No. 3, pp. 1151-1154.*
Hannibal et al, Journal of Bacteriology, Jul. 2000, pp. 3850-3853.

* cited by examiner

*Primary Examiner*—Hope Robinson
(74) *Attorney, Agent, or Firm*—Nixon & Vanderhye P.C.

(57) ABSTRACT

Isolated gene cluster involved in canthaxanthin biosynthesis, which comprises a polynucleotide wherein:
  crtY, crtI, crtB and crtW genes are clustered in this order and in the same orientation, and,
  preceding the four cited genes, crtE gene is oriented in the opposite direction.

Applications for producing natural carotenoids useful in pharmaceutical, cosmetic and nutritious compositions.

12 Claims, 3 Drawing Sheets

Canthaxanthin gene cluster of *Bradyrhizobium* ORS278

Astaxanthin gene cluster of *Agrobacterium aurantiacum*

Zeaxanthin gene cluster of *Flavobacterium* sp. R1534

Zeaxanthin diglucoside gene cluster of *Erwinia uredovora*

Zeaxanthin diglucoside gene cluster of *E. herbicola*

ISOLATED CAROTENOID BIOSYNTHESIS GENE CLUSTER INVOLVED IN CANTHAXANTHIN PRODUCTION AND APPLICATIONS THEREOF

This application claims the benefit of Provisional Application No. 60/297,272, filed Jun. 12, 2001, the entire content of which is hereby incorporated by reference in this application.

TECHNICAL FIELD

The present invention relates to an isolated carotenoid biosynthesis gene cluster involved in canthaxanthin production, such as obtained from the photosynthetic *Bradyrhizobium* sp. strain ORS278. This cluster includes five genes identified as crtE, crtY, crtI, crtB and crtW, the sequences of which are new. The present invention further relates to methods for producing carotenoids such as canthaxanthin or astaxanthin using the genes of the invention.

BACKGROUND OF THE INVENTION

Carotenoids are natural pigments that are responsible for many of yellow, orange and red colors seen in living organisms. Carotenoids are widely distributed in nature and have, in various living systems, two main biological functions. They serve as light-harvesting pigments in photosynthesis and they protect against photo-oxidative damages. Carotenoids have important commercial uses as coloring agents in the food industry since they are non toxic. The flesh, feathers or eggs of fish and bird assume the color of the dietary carotenoid provided and thus carotenoids are frequently used in dietary additives for poultry and in aquaculture. Moreover, carotenoids protect against damaging generated by near ultra violet (UV) radiations and in addition, have an anti-oxidative function. For all these reasons, carotenoids are important nutrious, cosmetic and pharmaceutical products and have a high economic value.

Over 600 different carotenoids have been described from carotenogenic organisms found among bacteria, yeast, fungi and plants. Currently only two of them, β-carotene and astaxanthin are commercially produced in microorganisms. β-carotene is obtained from algae and astaxanthin is produced in *Phaffia* yeast strain.

However, in the case of cultured products from *Phaffia* yeast, a great deal of expense is incurred for the gathering and extraction of astaxanthin, because said yeast has rigid cell walls and produces astaxanthin in a low yield. Also, in case of the cultured product of the green alga *Haematococcus*, not only the location for collecting sunlight, but an investment of a culturing apparatus for supplying an artificial light is required in order to supply light which is essential to the synthesis of carotenoids. For these reasons, carotenoids produced from biological source presently is inferior to that obtained by organic synthetic methods due to the cost. Organic synthetic methods, however, result in by-products. Thus, with a view to use them as a feed for fishes and shellfishes and an additive to foods, the products obtained by these organic synthetic methods are unacceptable due to the consumer's preference for natural products.

So, it is then desired to have genes that play a role in the biosynthesis of carotenoids, to produce carotenoids from microorganisms by introducing a gene or a gene cluster. No problem of by-products as a contaminants would thus be incurred. Moreover it would be considered not difficult to increase the production amount of carotenoids with gene manipulation to a level higher than that accomplished by the organic synthetic methods.

DISCLOSURE OF THE INVENTION

Figure 1:
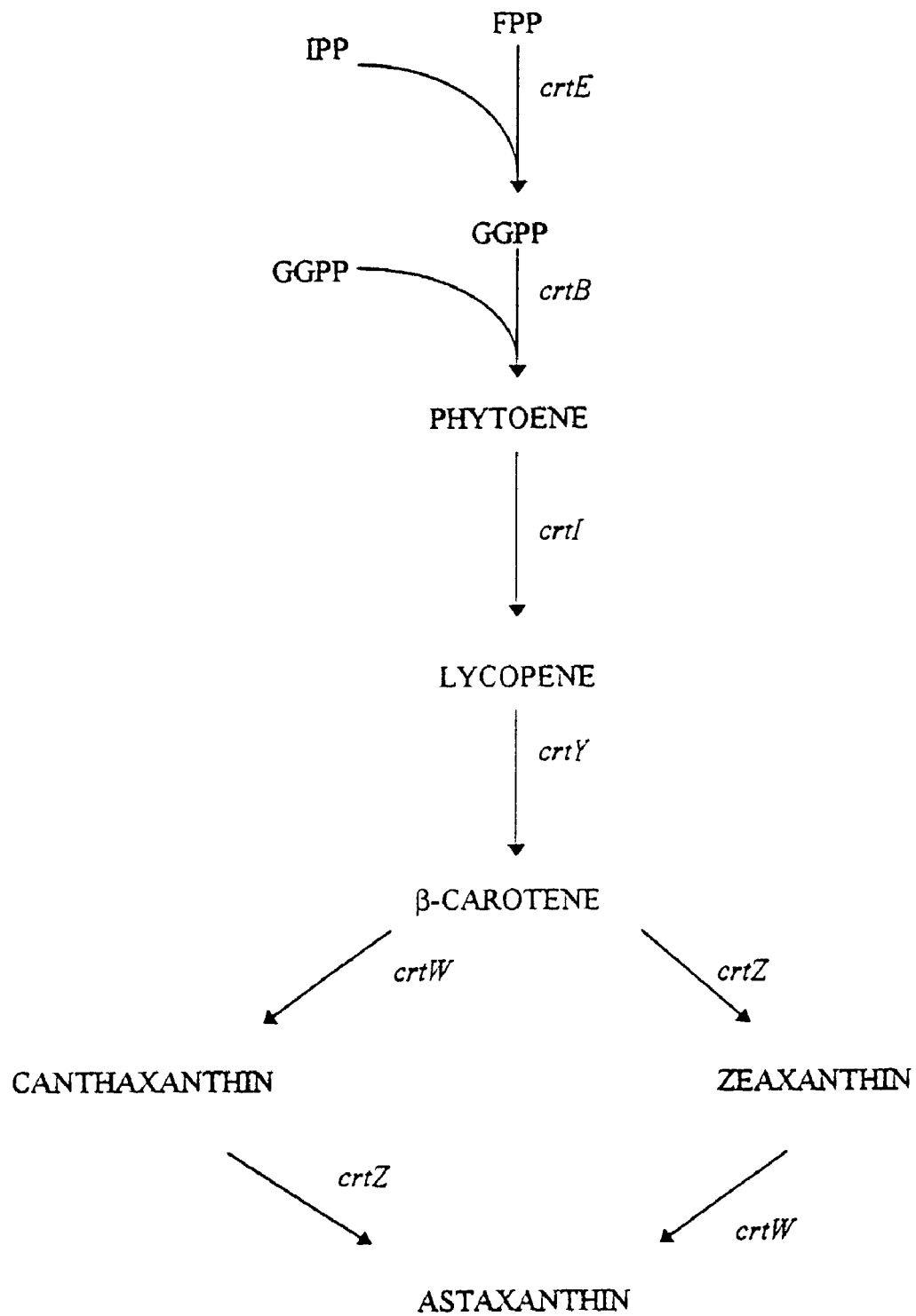
FIG. 1. Scheme of carothenoid biosynthesis pathways.

The object of the present invention is to provide an isolated gene cluster involved in canthaxanthin biosynthesis, genes comprised in such a cluster, and applications thereof. One object of the invention is to provide an isolated gene cluster involved in canthaxanthin biosynthesis, comprising a polynucleotide wherein:

crtY, crtI, crtB and crtW genes are clustered in this order and in the same orientation, and, preceding the four cited genes, crtE gene is oriented in the opposite direction.

Organisation of this cluster (see FIG. 2) is original. Even if crtY, crtI and crtB genes always occured in this order and were oriented in the same direction in the other cyclic carotenoid biosynthesis gene clusters (see FIG. 3), the location and the direction of crtE and in particular of crtW are specific of the present cluster.

Advantageously, said cluster comprises crtW gene which corresponds to sequence SEQ ID NO:1. In the same way, the crtY, crtE, crtB and crtI genes correspond to sequences SEQ ID NO: 2 to SEQ ID NO: 5 respectively.

In a preferred embodiment, the cluster of the invention is such as obtained by extraction from *Bradyrhizobium* sp. strain ORS278 (deposited Feb. 24. 1992 in the BCCM/LMG Bacteria Collection, Universiteit Gent-Laboratorium voor Microbiologie, K. L. Ledeganckstraat 35, 9000 Gent BELGIUM (Tel. 011 32 9 2645108) (outside the Budapest Treaty) under conditions of restricted distribution and allocated the accession number LMG 12187, and converted to Budapest Treaty deposit Jan. 25, 2006. *Bradyrhizobium* sp. strain ORS278 is a photosynthetic strain isolated from stem nodules of *Aeschymomene* species. This strain is subcultured as previously described (see Lorquin, J., <<Diversity of photosynthetic *Bradyrhizobium* strains from stem nodules of *Aeschymomene* species>>, p. 683-689, in R. Palacios. J. Mora, and W. E. Newton (ed), <<New horizon in nitrogen fixation>>, Kluwer Academic Publishers, Dordrecht, The Netherlands, 1993).

A further object of the invention is the isolated polynucleotides coding for the genes of the cluster. First, the present invention provides an isolated polynucleotide, the sequence of which corresponds to SEQ ID NO:1. This sequence codes for the CrtW protein. This is a new sequence since the highest percentage of amino acid identity compared with known CrtW proteins is 47%. Moreover, other isolated polynucleotides are provided, the sequences of which are selected from the group consisting of SEQ ID NO: 2 to SEQ ID NO: 5. These new sequences code for CrtY, CrtE, CrtB, CrtI proteins.

Consequently, the present invention also encompasses isolated polypeptides, the amino acid sequences of which correspond to sequences encoded, according to the universal genetic code and taking into account the degeneracy of this code, by at least one polynucleotide chosen from the group consisting of the gene cluster polynucleotide and the polynucleotide having the sequence SEQ ID NO: 1.

The present invention also includes a vector comprising at least a polynucleotide selected from the group consisting of gene cluster polynucleotide and the polynucleotides having sequences SEQ ID NO: 1 to SEQ ID NO: 5, preferably in the form of an expression vector.

Furthermore, it includes a cell transformed by genetic engineering comprising at least one polynucleotide chosen from the group consisting of the gene cluster polynucleotide and the polynucleotide having the sequence SEQ ID NO: 1 and more specifically a cell transformed by genetic engineering to produce at least one polypeptide the amino acid sequence of which corresponds to a sequence encoded, according to the universal genetic code and taking into account the degeneracy of this code, by at least one polynucleotide chosen from the group consisting of the gene cluster polynucleotide and the polynucleotide having the sequence SEQ ID NO:1. In particular, such a cell can be a recombinant cell comprising a host cell which is transformed by the aforesaid polynucleotide, preferably by a vector comprising said polynucleotide. More preferably said host cell is a prokaryotic cell and more preferably, said host cell is $E.\ coli$. However, said host cell may also be an eukaryotic cell, preferably a yeast cell, a fungal cell or a plant cell.

Preferably, said plant cell is used to create a plant transformed by genetic engineering, which produce at least one carotenoid.

Said clusters and polynucleotides are advantageously used for producing carotenoids.

Accordingly, the present invention further provides methods for production of carotenoids, such as, but not limited to, β-carotene, canthaxanthin, zeaxanthin and astaxanthin, these methods comprising culturing a host cell such as above defined in a nutrient medium including sources of carbon, nitrogen and inorganic substances; and recovering an individual carotenoid, a mixture of carotenoids or a specific protein from the host cell and/or the growth medium.

One aspect of the invention is a method for producing at least one carotenoid, comprising:
the production of a plasmid containing a polynucleotide selected from the group consisting of gene cluster polynucleotide and the polynucleotides corresponding to SEQ ID NO:1 to SEQ ID NO: 5;
the transfection of a host cell as above defined by said plasmid;
the culture of said cell and the recovery of produced carotenoids.

In particular, the invention encompasses a method for producing at least one carotenoid, comprising:
the production of a plasmid containing a polynucleotide selected from the group consisting of gene cluster polynucleotide and the polynucleotides corresponding to SEQ ID NO:1 to SEQ ID NO:5, activated by a promoter, in order to overproduce said polynucleotide,
the transfection of $Bradyrhizobium$ sp. strain ORS278 by said plasmid,
the culture of said strain and the recovery of produced carotenoids.

Preferably, a further aspect of the invention is a method for producing at least astaxanthin, comprising:
the production of a plasmid containing the polynucleotide selected from the group consisting of gene cluster polynucleotide and the polynucleotide of SEQ ID NO: 1;
the transfection of a host cell comprising at least crtZ gene, by said plasmid;
the culture of said host cell and the recovery of produced astaxanthin.

Another aspect of the invention is a method for producing at least one carotenoid, by enzymatic transformation, comprising:
the production of a plasmid containing the polynucleotide the sequence of which is SEQ ID NO: 1
the transfection of a host cell to overproduce CrtW protein,
the immobilization of said protein on a column
the percolation of a carotenoid solution and the recovery of the percolated solution.

In particular, the carotenoid solution is a β-carotene or a zeaxanthin solution.

The carotenoids such obtained are useful in various applications of interest.

The present invention thus relates to a pharmaceutical composition comprising an efficient amount of at least one carotenoid synthetized by a cell transformed by genetic engineering as above described, in association with a pharmaceutically acceptable carrier.

The present invention also includes a method for treating cancer by using a pharmaceutical anti-oxidant composition comprising an efficient amount of at least one carotenoid synthetized by a cell transformed by genetic engineering as above described in association with a pharmaceutically acceptable carrier.

According to another application, the invention relates to a cosmetic composition comprising at least one carotenoid synthetized by a cell transformed by genetic engineering as above described, in particular, a tanning product and/or a dermal protection composition, with the usual carriers.

In still another application, the invention relates to a nutritious composition comprising at least one carotenoid synthetized by a cell transformed by genetic engineering as above described, preferably a feed additive for cultured fishes or shellfishes or a food additives.

Other characteristics and advantages of the invention are given in the following examples with reference to said figures.

EXAMPLE 1

Isolation of Probe A.

Genes crtB and crtI, encoding phytoene synthase and phytoene desaturase, respectively, two enzymes involved in the initial steps of carotenoid biosynthesis (FIG. 1), have been isolated and characterized in various microorganisms. Having compared the deduced amino acid sequences of the CrtI and CrtB proteins from $Erwinia\ uredovora$, $Flavobacterium$ sp. strain ATCC 21588, $Rhodobacter\ sphaeroides$, and $Agrobacterium\ aurantiacum$, specific motifs were chosen for designing the degenerated primers CrtIf (SEQ ID NO:6) and CrtBr (SEQ ID NO:7). PCR amplification was performed with a Perkin-Elmer model 2400 thermocycler in a 50 μl (total volume) reaction mixture containing 100 ng of strain ORS278 genomic DNA, each deoxynucleotide triphosphate (200 μM), primers (0.8 μM each), MgCl$_2$ (1.5 mM), 1.25 of Taq DNA polymerase (Promega, France), and buffer supplied with the enzyme. A touchdown PCR was done as follows: initial denaturation at 94° C. for 5 min followed by 20 cycles consisting of a 30 s denaturation at 94° C., 30 s at an annealing temperature of 60 to 50° C., and a 1 min primer extension at 72° C., followed by 15 cycles consisting of a 30 s denaturation at 94° C., 30 s at an annealing temperature at 50° C., and a 1 min primer extension at 72° C. After the final elongation step at 72° C. for 7 min, the amplified 408 bp fragment obtained (probe A, SEQ ID NO:8) was purified by a Wizard procedure and was ligated into a pGEM-T vector (Promega, France). The ABI Prism BigDye Terminator Cycle Sequence Kit (Applied Biosystems, California) was used to sequence the cloned PCR product with the universal oligonucleotide M13 forward and M13 reverse. Sequencing reactions were analyzed on an Applied Biosystems model 310 DNA sequencer.

EXAMPLE 2

Isolation of Canthaxanthin Gene Cluster

Two specific primers, CrtIBfow.ORS278 (SEQ ID NO:9) and CrtIBrev.ORS278 (SEQ ID NO:10), based on the sequence of the amplified DNA fragment, were designed for PCR screening of a library of the ORS278 strain constructed with the SuperCos I cosmid vector kit (Stratagene, Calif.), as instructed by the manufacturer. Four positive clones were isolated and confirmed by Southern blot analysis by using the 408 bp fragment as a probe. Clone pSTM73, containing an insert of approximately 35 kb, was used to characterize this crt gene cluster.

Figure 2:
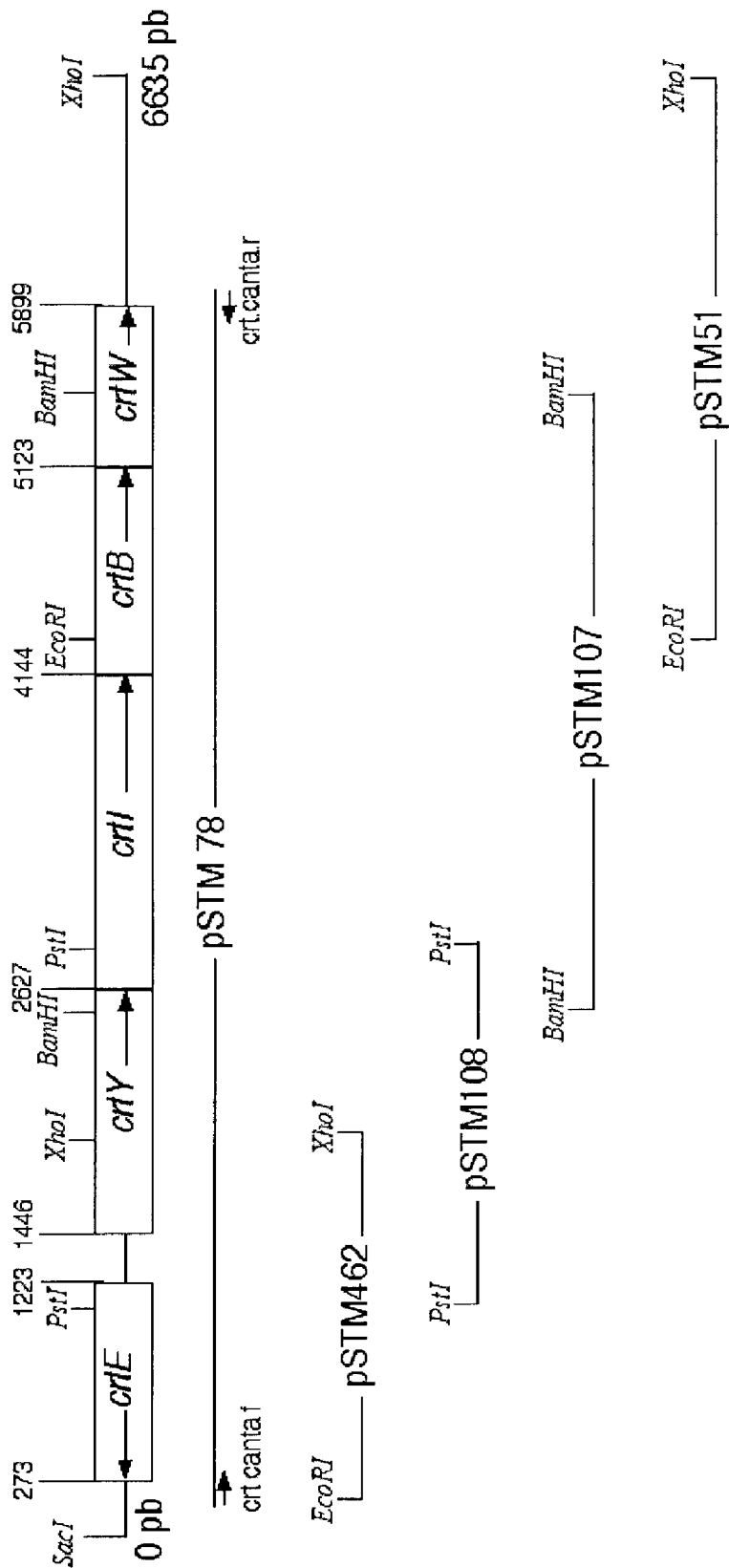
FIG. 2. Organization of the canthaxanthin biosynthesis gene cluster of *Bradyrhizobium* sp. strain ORS278 and locations of various subcloned fragments.

A 6.5 kb region in the inserted DNA fragment of pSTM73 cosmid, showing a positive hybridization signal to probe A, was sequenced and analyzed as shown in FIG. 2. This figure relates to the organization of the canthaxanthin gene cluster of Bradyrhizobium sp. strain ORS278 and the locations of various subcloned fragments. The restriction fragments are inserted into pUC18 (pSTM108, pSTM107, and pSTM51) or pUC19 (pSTM462), the crt genes are transcribed from the lac promoter of the vector. In the plasmid pSTM78, the insert was obtained by Long PCR using the primers Crt-.canta.f (SEQ ID NO:11) and Crt.canta.r (SEQ ID NO:12) and was cloned into pGEM-T (Promega, France). In pSTM78, the crtY, crtI, crtB and crtW genes are under the lac promoter control.

Figure 3:
FIG. 3. Comparison of the organization of the cyclic carotenoid gene clusters, of *Bradyrhizobium* sp. strain ORS278, *Agrobacterium aurantiacum*, *Flavobacterium* sp. Strain R1534, *Erwinia uredovora*, and *Erwinia herbicola*.
Figure 3:
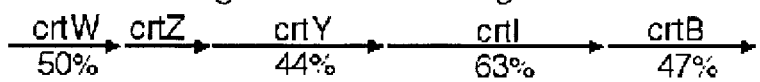
Figure 3:
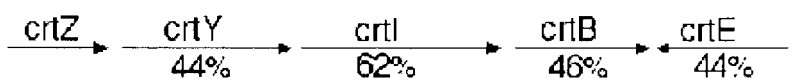
Figure 3:
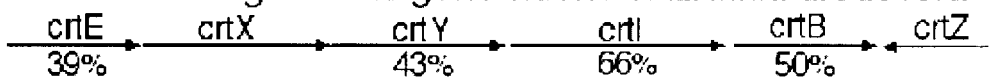
Figure 3:
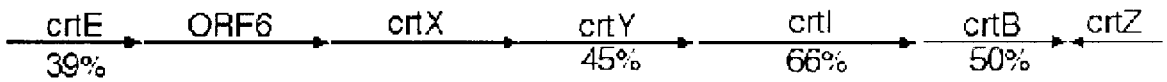

This nucleotide sequence had five open reading frames (ORFs) encoding proteins with similarity to known Crt enzyme. Based on this similarity, ORFs was assigned to crtY, crtI, crtB, crtE and crtW genes. This CRT gene cluster involved in canthaxanthin synthesis was isolated. Four of the five ORFs, identified as crtY, crtI, crtB and crtW, were found to be clustered in this order in the same orientation, whereas the crtE ORF preceded said four ORFs, but was in the opposite direction, as shown in FIG. 3. This figure illustrates a comparison of the organization of cyclic carotenoid gene clusters of Bradyrhizobium sp. strain ORS278, *A. aurantiacum*, *Flavobacterium* sp. Strain R1534, *E. uredovora*, and *E. herbicola*. Arrows represent the orientation of ORFs. The percentage values below the genes indicate the percentage of amino acid identity compared to Bradyrhizobium sp. strain ORS278.

EXAMPLE 3

Carotenoid Production in *Escherichia coli* Transformants.

To check the functionality of the different ORFs identified in strain ORS278, several carotenoid-accumulating *E. coli* transformants were complemented with plasmids carrying various crt genes of strain ORS278 and carotenoids synthesized were analyzed by high-pressure liquid chromatography (see Table 1, below). The conditions were as follows: 5 µm Hypersil $C_{18}$ column (250 by 4.6 mm; Alltech, France), eluent of acetonitrile-methanol-isopropanol (85/10/5, vol/vol/vol), flow rate of 1 ml/min, and detection at 470 nm (450 nm for β-carotene). Peaks were compared and coeluted with standard compounds then identified by their visible spectra and partition coefficients.

TABLE 1

Analysis of carotenoids accumulated in *E. coli* transformants carrying various combinations of crt genes from *E. uredovora* and Bradyrhizobium sp. strain ORS278[a].

| *E. Coli* host strain characteristics | | *E. coli* tranformant characteristics after complementation | |
| --- | --- | --- | --- |
| Plasmid (crt genes of *E. uredovora* carried) | Carotenoid accumulated | Plasmid introduced[c] (crt genes of ORS278 carried) | Carotenoid accumulated[d][e] |
| None | —[f] | pSTM73 (crtE crtY crtI crtB crtW) | — |
| None | — | pSTM78 (crtE crtY crtI crtB crtW) | — |
| pACCRT-E[b] (crtE) | GGPP | pSTM78 (crtE crtY crtI crtB crtW) | Canthaxanthin (100%) [95.4] |
| pSTM420 (crtI crtB crtY) | — | pSTM462 (crtE) | β-Carotene (98%), nic[g] (2%) |
| pACCRT-E[b] (crtE) | GGPP | pSTM107 (crtI crtB) | Lycopene (100%) |
| pACCRT-EB[b] (crtE crtB) | Phytoene | pSTM107 (crtI crtB) | Lycopene (100%) |
| pACCRT-EIB[b] (crtE crtI crtB) | Lycopene | pSTM108 (crtY) | β-Carotene (100%) |
| pACCRT-EIBY[b] (crtE crtI crtB crtY) | β-Carotene | pSTM51 (crtW) | Canthaxanthin (90%) [800], echinenome (2%), nic (8%) |

[a]Transformants were grown in Luria-Bertani medium for 36 h in the presence of ampicillin (50µg/ml), chloramphenicol (30 µg/ml), and 0.125 mM isopropyl-1-thio-β-D-galactopyranoside.
[b]The plasmids used were obtained according to the prior art. Plasmid pSTM420 was obtained after deletion by SalI digestion of the crtE gene from the plasmid pACCRT-EIBY.
[c]Details on insertion of the various constructed plasmids are presented in FIG. 2.
[d]The percentage of the accumulated carotenoid of the total carotenoid content is indicated in parentheses.
[e]In square brackets, total (cis plus trans) canthaxanthin level is indicated in micrograms per gram of dry cell weight.
[f]"—", carotenoids not detected.
[g]"nic", non identified compound.

When plasmid pSTM78 carrying the complete crt cluster of Bradyrhizobium sp. strain ORS278 was introduced into the *E. coli* transformant that had accumulated geranylgeranyl pyrophosphate (GGPP) as a result of the presence of the crtE gene of *E. uredovora*, the new transformant obtained was shown to accumulate canthaxanthin. This result indicates that the crtY, crtI, crtB, and crtW genes are functional and allow the production of canthaxanthin in *E. coli*. When plasmid pSTM462 carrying the crtE gene of *Bradyrhizobium* sp. strain ORS278 under the lac promoter was introduced into the *E. coli* transformant containing the crtI, crtB, and crtY genes of *E. uredovora,* the new transformant accumulated β-carotene, showing the functionality of the crtE gene.

EXAMPLE 4

Poultry feed: The conventional ingredients include wheat, maize, barley, sorghum, oats, rice and/or soybean meal, usually in ground or broken form, in major proportions. Further ingredients in minor amounts include fish, meat and/or bone meal, wheat bran, straw, yeast, hydrolyzed fat, tallow, lard, limestone, salt, methionin premix, mineral premix, vitamin premix and/or anticaking agent. Any poultry feed can be enriched with at least one of the carotenoids produced by the invention, from 1 to 20 percent by weight.

| Ingredients | Content in weight percent |
|---|---|
| Wheat | 40.00 |
| Maize | 10.00 |
| Oats | 10.00 |
| Soybean meal | 10.00 |
| Limestone | 10.00 |
| Carotenoid | 6.00 |
| Fish meal | 5.00 |
| Meat meal | 5.00 |
| Hydrolysed fat | 2.00 |
| Yeast | 1.00 |
| Methionin premix | 0.50 |
| Salt | 0.20 |
| Mineral premix | 0.20 |
| Vitamin premix | 0.10 |

Fish or shell fishes feed: Typical ingredients include fish meal, wheat and bone meal, soybean meal, wheat flour, cooked starch, yeast, fish oil, soybean oil, soya lecithin, methionin, vitamins and minerals. Carotenoids are added in the same proportion as the poultry feed.

Feed composition: Feed can be produced by conventional methods, involving physical admixture, pelleting, extrusion, microencapsulation, spraying etc.

What is claimed is:

1. An isolated gene cluster comprising an isolated polynucleotide wherein:
   crtY, crtI, crtB and crtW genes are clustered in this order and in the same orientation, and,
   preceding the four cited genes, crtE gene is oriented in the opposite direction, said crtW gene of the polynucleotide being SEQ ID NO:1, and
   said crtY, crtE, crtB and crtI genes of the polynucleotide being SEQ ID NO:2 to SEQ ID NO:5, respectively.

2. An isolated gene cluster according to claim 1, obtained by extraction from *Bradyrhizobium* sp. strain ORS278.

3. An isolated polynucleotide consisting of SEQ ID NO:1.

4. A vector comprising at least an isolated polynucleotide according to claim 1 or claim 3.

5. A cell transformed by genetic engineering comprising:
   (i) a polynucleotide according to claim 1;
   (ii) a polynucleotide according to claim 3 or
   (iii) a polynucleotide according to claim 1 and a polynucleotide according to claim 3,
   wherein said cell is an isolated cell.

6. A cell transformed by genetic engineering to produce at least one polypeptide, the amino acid sequence of which corresponds to the sequence encoded, according to the universal genetic code and taking into account the degeneracy of this code, by:
   (i) a polynucleotide according to claim 1;
   (ii) a polynucleotide according to claim 3; or
   (iii) a polynucleotide according to claim 1 and a polynucleotide according to claim 3,
   wherein said cell is an isolated cell.

7. A method for producing at least one carotenoid, comprising:
   producing a plasmid containing the polynucleotide according to claim 1;
   transfecting an isolated host cell with said plasmid; and
   culturing the transfected isolated host cell in a manner whereby said at least one carotenoid is produced and recovering said at least one carotenoid.

8. A method for producing at least one carotenoid, comprising:
   producing a plasmid containing the polynucleotide according to claim 1 activated by a promoter, in order to over produce said polynucleotide;
   transfecting a *Bradyrhizobium* sp. strain ORS278 with said plasmid;
   culturing said strain in a manner whereby said at least one carotenoid is produced and recovering said at least one carotenoid.

9. A method for producing at least one astaxanthin, comprising:
   producing a plasmid containing the polynucleotide according to claim 1;
   transfecting an isolated host cell comprising a crtZ gene, with said plasmid;
   culturing said transfected isolated host cell in a manner whereby said at least one astaxanthin is produced; and
   recovering said at least one astaxanthin.

10. A method for producing at least one carotenoid, by enzymatic transformation, comprising:
    producing a plasmid comprising the polynucleotide according to claim 3;
    transfecting an isolated host cell to overproduce crtW protein encoded by said polynucleotide;
    immobilizing said protein on a column to produce an immobilized column;
    percolating a carotenoid solution on said immobilized column and recovering the percolated solution.

11. A method according to claim 10, wherein the carotenoid solution is a β-carotene or a zeaxanthin solution.

12. An isolated gene cluster comprising one of SEQ ID NO:1, SEQ ID NO:2, SEQ ID NO:3, SEQ ID NO:4, and SEQ ID NO:5.

* * * * *

SEQUENCE LISTING

```
<160> NUMBER OF SEQ ID NOS: 12

<210> SEQ ID NO 1
<211> LENGTH: 777
<212> TYPE: DNA
<213> ORGANISM: Artificial Sequence
<220> FEATURE:
<223> OTHER INFORMATION: Description of Artificial Sequence: crtW

<400> SEQUENCE: 1
atgcatgcag caaccgccaa ggctactgag ttcggggcct ctcggcgcga cgatgcgagg      60
cagcgccgcg tcggtctcac gctggccgcg gtcatcatcg ccgcctggct ggtgctgcat     120
gtcggtctga tgttcttctg gccgctgacc cttcacagcc tgctgccggc tttgcctctg     180
gtggtgctgc agacctggct ctatgtaggc ctgttcatca tcgcgcatga ctgcatgcac     240
ggctcgctgg tgccgttcaa gccgcaggtc aaccgccgta tcggacagct ctgcctgttc     300
ctctatgccg ggttctcctt cgacgctctc aatgtcgagc accacaagca tcaccgccat     360
cccggcacgg ccgaggatcc cgatttcgac gaggtgccgc cgcacggctt ctggcactgg     420
ttcgccagct ttttcctgca ctatttcggc tggaagcagg tcgcgatcat cgcagccgtc     480
tcgctggttt atcagctcgt cttcgccgtt cccttgcaga acatcctgct gttctgggcg     540
ctgcccgggc tgctgtcggc gctgcagctg ttcaccttcg gcacctatct gccgcacaag     600
ccggccacgc agcccttcgc cgatcgccac aacgcgcgga cgagcgaatt tcccgcgtgg     660
ctgtcgctgc tgacctgctt ccacttcggc tttcatcacg agcatcatct gcatcccgat     720
gcgccgtggt ggcggctgcc ggagatcaag cggcgggccc tggaaaggcg tgactaa      777
```

`<210>` SEQ ID NO 2

-continued

<211> LENGTH: 1185
<212> TYPE: DNA
<213> ORGANISM: Artificial Sequence
<220> FEATURE:
<223> OTHER INFORMATION: Description of Artificial Sequence: crtY

<400> SEQUENCE: 2

| | | | | |
|---|---|---|---|---|
| atgagtcgag atgccgacgt catcgtcatc ggcggcggtc ttgccggctg cctgatcgcc | 60 |
| ttgcggctca ccgacgcacg gccggatctg cgcgtcgtca tcatcgaagg ctcggccagc | 120 |
| atcgccggca atcacacctg gagcttcttt ggaaccgata tctcgtccga ccagcacgcc | 180 |
| tggctcggac ggctcgtcgg tcatcgctgg ccggggttatg aggtgcgctt cgccgaacat | 240 |
| gccatccgtc tgtcgaccgc ctacctctcc atgacgtcga cgcggctgcg tgccgaggtc | 300 |
| gagcagcgtt tccggagag gatcctgcgc gacgcgacgg ccatctccgc aacggcagac | 360 |
| catgtcgtgc tggagggcgg ccgcaccttg cgcgcgccct gcgtgatcga tgcgcgcggc | 420 |
| ggccggccgg tgccggggct cgctctcggg tttcagaagt tcctcgggct cgaggtgcgg | 480 |
| ctggccgcgc cgcacggcct cgatgtgccc atcgtgatgg acgcgacggt cgcgcagagc | 540 |
| gacggctatc gcttcgtcta cacgctgccg ctcgaccctc agcggctgtt gatcgaggac | 600 |
| acctactata gcgacggcgg cgagttgccc gagcaggtgc tgcatcagcg catcgcgcgc | 660 |
| tacgcgctcg ccaagggctg gcagatcgcc gagatcatcc gcgcggagca gggtgtgctg | 720 |
| cccgtcattc tggcgggcga tccgtccggg ctggtcagca gcccgacag cccgccgcgc | 780 |
| gtgggtctcg cggcgcttct cgtgcatccg acgaccggct attcgctgcc ggacgcggtc | 840 |
| cgcgtcgccg atctgctgac ggcgcggctt gcgcaacggg gcgcgctctc gagcgctgac | 900 |
| gcgcgcgaga cgatcgatgg ctacggccgg acgatctggc gccggcgcgg ctactatcgc | 960 |
| ttcctgaacc ggatgctgtt caaggccgcc gagccctccg agcgtcaccg aatcctggca | 1020 |
| cgattttacg gtctcgatca ggccctgatc gagcgcttct acgccgcccg gatccagccg | 1080 |
| caggacaagc tgcgcgtctt catgcatatg ctgatgaagc cgccgatccc gatctcgtcc | 1140 |
| gcgctcgcct gcctgcctga ggcgagcgcc ttcaagaccc catga | 1185 |

<210> SEQ ID NO 3
<211> LENGTH: 951
<212> TYPE: DNA
<213> ORGANISM: Artificial Sequence
<220> FEATURE:
<223> OTHER INFORMATION: Description of Artificial Sequence: crtE

<400> SEQUENCE: 3

| | | | | |
|---|---|---|---|---|
| atgcacaaac ccgtcgacct caccgatacg gcggccttcg agacccagct cgatcgttgg | 60 |
| cggggacgca tcggcgaagc ggttgccgag gccatggcat cggcacgac ggttccggcc | 120 |
| ccgctgcagg cgggcatgag ccacgcagtc ctggcgggcg gcaagagata ccgcggcatg | 180 |
| ctcgtgctcg cgctcggatc ggacctcggc gtgcccgagg agcagctttt gtcgtcggct | 240 |
| gtggctattg agaccattca tgcagcctcc ctcgtggtcg atgatcttcc ctgcatggac | 300 |
| gacgcgcggc ggcgacggtc gcagccggcg acgcatgtcg cgttcggcga ggccacagca | 360 |
| atcctcagca gcatcgccct gatcgcccgc gcgatggagg tcgtggcgag ggaccggcaa | 420 |
| ctttcgcccg cctcccgcag ttccatcgtg acactctgt cgcacgccat cggcccgcag | 480 |
| gcccttttgtg gcgggcaata tgacgatctc tatcctccct actacgcgac cgagcaggat | 540 |
| ctgatccatc gctatcaacg caagaccagc gcgctgtttg tcgcagcgtt ccgctgcccc | 600 |
| gcgctcctcg cggaggtgga tccggagacg ctgctgcgca tcgcccgcgc gggccagcgg | 660 |

```
ctcggcgtcg catttcagat attcgacgat ctcctcgacc tgacaggcga tgcccatgca    720
atcggcaagg atgtcggcca ggaccatggc accgtgacgc tcgccacgct gctcggaccc    780
gcgcgggcgg ccgaacgggc ggcggatgag cttgcggccg tgcagaagga actgcgcgag    840
acggtcggcc ccgggcgcgc cctcgacctg atcaggcgga tggccgcacg catcgccggc    900
accggcaaga atccgccgg acgcgacgat ctgcggccgc atgccggctg a              951
```

```
<210> SEQ ID NO 4
<211> LENGTH: 1008
<212> TYPE: DNA
<213> ORGANISM: Artificial Sequence
<220> FEATURE:
<223> OTHER INFORMATION: Description of Artificial Sequence: crtB

<400> SEQUENCE: 4
atgacgctgc gcgacaatga ccatctggcg cggctgagcg aagccgtcat ccgcaacggc     60
tcgaagagtt tcgcagccgc atccaagctg ttcgattccc gcacccgtgc cagcgtgcac    120
ctgctctacg cctggtgccg gcattgcgac gacgtcatcg acggacagga tctcggaatt    180
cggcagggcg tcggcgcgcc tggcccgcag atcgggactt tgcagatgct gcgcgaccag    240
acggcgcagg cgctggaggg ggcgccgatg cgcgatccgg tgttccaggg attgcagcgc    300
gtcgtgcagg agcacgcgat tccgcaccat cacgtgttcg agctgctcga cggcttcgcc    360
atggatgtcg acggcgcgga atacgagacg ctgagcgaga cgctggacta ctgctatcac    420
gtggccggcg tggtcggcgt gatgatgtcg gcgatcatgg gcgctcgcga ggaggcgacg    480
ctggaccgcg cggccgatct cggcatcgcg ctgcagctca ccaacatcgc ccgtgacgtg    540
atcgaggatg cccagaccgg ccgcatgtat ctgccgcagc aatggctgtg cgaggccggc    600
gtgccggccg ccgaggtcgc ggaaccgcag catcggcagg cggtgttccg tgtcgtcgcg    660
cggctgctcg atgtcgcgga gcagtttttac gaggccagcg aggcaggcat cgcccggctg    720
ccggtgcgtt gcgcctgggc ggtggagacg gcccgcgtcg tctatcgcca gatcgggcgc    780
gaggtgatga gcgcggtcc cggcgcctgg gacgcccgca tcgccacgac aggcgcgcag    840
aagctcggcg cgatcggccg cagcgcattg acgcttggtc tcacccgcac ctgggttaag    900
gtgcccgcgc gcgagcacaa cctctggacc cgcccgaagg cgcggcgcgc cgccagtgac    960
gcacaagcga gctttgccaa tgcatgcagc aaccgccaag gctactga                1008
```

```
<210> SEQ ID NO 5
<211> LENGTH: 1521
<212> TYPE: DNA
<213> ORGANISM: Artificial Sequence
<220> FEATURE:
<223> OTHER INFORMATION: Description of Artificial Sequence: crtI

<400> SEQUENCE: 5
atgagtcaag agatgcagaa cgccaagaca gcagtggtga tcggttcggg atttggtggg    60 cttttcgctcg ccatacgcct gcaatcggcc gggatcgcga caacgctcgt cgagaagcgc    120
gacaagttcg gcggccgcgc ctatgtctac gagcaggacg gcttcacctt cgacgccggg    180
cccactgtca tcaccgatcc gacctgcctg caggagctgt tcgcgctctc ggggcgcaag    240
ctcgagaact atgtcgagct gatgccggtc tccccattct atcagctgcg ctgggaggac    300
ggcgccactt tcgactacgt caacgaccag gccgagctgg agcgccagat cgcggcgttc    360
tgtccggctg atgtggacgg ctatcggcgc ttccggtcgt atagcgagcg cctgctggag    420
```

```
gagggctacg tcaagctcgg ccacgtgccg ttcccggatt tccggagcat ggtgcgtgtg    480
gcgccgcagc tggtggcgct gcagagctat cgcagcgtct atagcaaggt gtcgcaatac    540
gtctccgacg agcatctgcg gcaggccttc agcttccact cgctgctggt cggcggcaat    600
ccgttcgcga cgtcctcgat ctacgcgctg atccatgcgc tggagcgccg ctggggagtc    660
tggttcccgc gcggcggcac cggcgcgctc atcaacaagg gctcgtcca gctgttcaag    720 gatctcggcg gcgaggtgac gctgtcgacc agcgtgagcc ggatcgagac ggcgaacggg    780
cgggtcagtg ccgtggtcgc cgaggacggc cgtcggttcg ccgccgacat cgtcgccagc    840
aacgccgacg tcgttcatac ctaccgcgat ctcctgaagg acgagccgct ggcgcggccg    900
acggcgcaat ctttgatgcg caagcgcttc agcatgtcgc tgttcgtgat ctatttcggc    960 ctgccgccgcg agcatccgga gctcaagcac cacatcattc tgttcggccg cgctaccgcg   1020
gagctgatca acgagatctt caaggggccc gcgttgcctg aggatttctc gctgtatctg   1080
cacgcgccga gcgtgaccga tccgtcgctc gcgccacaag gctgcagcac ctattacgtg   1140
ctctcgccgg tgccgcatct cgccgccgca ccgatcgact ggagcgtgga gggcccgcgc   1200
tatcgcgacc gcatcctcga ctatctcgag gcgcgcattc tgccggggct gaagtcggac   1260
ctcgccacct gccgcatctt cacgccgcag gatttcaaca ccgagctgaa tgcgcatctc   1320
ggctccgcgt tctcgctgga gccgatcctg acgcagagcg cgtatttccg cgcccacaac   1380
gcggacgaca agatcaaggg gctgtatctc gtcggcgccg gcacccatcc gggcgccggc   1440
attcccggcg tcgtcggctc ggccaaggcg accgcgcgag tcatcctcga ggaccagcgc   1500
gaactcgcgg aggcgcaatg a                                             1521

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: crtIf
<220> FEATURE:
<221> NAME/KEY: misc_feature
<222> LOCATION: (3)
<223> OTHER INFORMATION: A, T, G or C
<220> FEATURE:
<221> NAME/KEY: misc_feature
<222> LOCATION: (6)
<223> OTHER INFORMATION: A, T, G or C
<220> FEATURE:
<221> NAME/KEY: misc_feature
<222> LOCATION: (15)
<223> OTHER INFORMATION: A, T, G or C

<400> SEQUENCE: 6
gtnggngcrg gcacncaycc                                                 20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:  CrtBr

<400> SEQUENCE: 7
tcgcgrgcra trttsgtsar rtg                                             23

<210> SEQ ID NO 8
<211> LENGTH: 408
<212> TYPE: DNA
<213> ORGANISM: Artificial Sequence
```

```
<220> FEATURE:
<223> OTHER INFORMATION: Description of Artificial Sequence: probe A

<400> SEQUENCE: 8
attcgcagcg gctcgaagag tttcgcagcc gcatccaagc tgttcgattc ccgcacccgt      60
gccagcgtgc acctgctcta cgcctggtgc cggcattgcg acgacgtcat cgacggacag     120
gatctcggaa ttcggcaggg cgtcggcgcg cctggcccgc agatcgggac tttgcagatg     180
ctgcgcgacc agacggcgca ggcgctggag ggggcgccga tgcgcgatcc ggtgttccag     240
ggattgcagc gcgtcgtgca ggagcacgcg attccgcacc atcacgtgtt cgagctgctc     300
gacggcttcg ccatggatgt cgacgggcgc gaatacgaga cgctgagcga gacgctggac     360
tactgctatc acgtggccgg cgtggtcggc gtgatgatgt cggcgatc                  408

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      CrtIBfow.ORS278

<400> SEQUENCE: 9
attcgcagcg gctcgaagag                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      CrtIBrev.ORS278

<400> SEQUENCE: 10
gatcgccgac atcatcacgc                                                  20

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Crt.canta.f

<400> SEQUENCE: 11
gcaaccggta cccgagttaa ttcgctcgga atg                                   33

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Crt.canta.r

<400> SEQUENCE: 12
atggtgaagc ttatgcggca gcgggtttag tc                                    32
```